United States Patent
Zar et al.

(10) Patent No.: US 11,457,995 B2
(45) Date of Patent: Oct. 4, 2022

(54) ACCURATE BALLOON COMPUTATION AND VISUALIZATION

(71) Applicant: Biosense Webster (Israel) Ltd., Yokneam (IL)

(72) Inventors: Lior Zar, Poria Illit (IL); Turgeman Aharon, Zichron Ya'acov (IL); Natan Sharon Katz, Atlit (IL); Benjamin Cohen, Haifa (IL); Limor Provizor, Lavon (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 851 days.

(21) Appl. No.: 16/234,150

(22) Filed: Dec. 27, 2018

(65) Prior Publication Data

US 2020/0205932 A1 Jul. 2, 2020

(51) Int. Cl.
*A61B 90/00* (2016.01)
*A61B 34/10* (2016.01)
(Continued)

(52) U.S. Cl.
CPC .......... *A61B 90/37* (2016.02); *A61B 18/1492* (2013.01); *A61B 34/10* (2016.02); *A61M 25/0127* (2013.01); *G06T 15/20* (2013.01); *A61B 2018/0022* (2013.01); *A61B 2018/00357* (2013.01); *A61B 2018/00577* (2013.01); *A61B 2034/102* (2016.02);
(Continued)

(58) Field of Classification Search
CPC ..... A61B 90/37; A61B 34/10; A61B 18/1492; A61B 2018/0022; A61B 2018/00357; A61B 2018/00577; G06T 15/20
See application file for complete search history.

(56) References Cited

U.S. PATENT DOCUMENTS 6,592,520 B1 7/2003 Peszynski et al.
10,820,941 B2 * 11/2020 Gelbart ................ A61B 5/6858
(Continued)

FOREIGN PATENT DOCUMENTS

WO WO 2018/191149 A1 10/2018

OTHER PUBLICATIONS

EP Search Report dated May 11, 2020, Application No. EP 19 21 7957.
(Continued)

*Primary Examiner* — Michael F Peffley
*Assistant Examiner* — Bo Ouyang

(57) ABSTRACT

A system includes a balloon catheter having a shaft, an inflatable balloon fitted at a distal end of the shaft, and multiple electrodes disposed on the inflatable balloon, a display, and a processor configured to receive signals that are indicative of respective electrode positions of the multiple electrodes in 3D space, compute the respective electrode positions of the multiple electrodes based on the received signals, from among a plurality of virtual planes defined by different respective groups of the electrode positions, select a virtual plane that contains a maximum number of the electrode positions to within a given tolerance, fit a virtual circle to the electrode positions that are within the given tolerance of the selected virtual plane, and render to the display a 3D representation of the balloon catheter based on a position and orientation of the fitted virtual circle in 3D space.

23 Claims, 5 Drawing Sheets

(51) Int. Cl.
  *A61B 18/14* (2006.01)
  *A61M 25/01* (2006.01)
  *G06T 15/20* (2011.01)
  *A61B 34/20* (2016.01)
  *A61B 18/00* (2006.01)

(52) U.S. Cl.
  CPC . *A61B 2034/2065* (2016.02); *A61B 2090/367* (2016.02); *A61M 2025/0166* (2013.01); *G06T 2210/41* (2013.01); *G06T 2215/16* (2013.01)

(56) References Cited

U.S. PATENT DOCUMENTS

| | | |
|---|---|---|
| 2009/0264738 A1 | 10/2009 | Markowitz et al. |
| 2010/0317962 A1 | 12/2010 | Jenkins et al. |
| 2014/0095105 A1 | 4/2014 | Koyrakh et al. |
| 2018/0280080 A1 | 10/2018 | Govari et al. |
| 2019/0350489 A1* | 11/2019 | Ludwin ............... A61B 5/6853 |

OTHER PUBLICATIONS

Richard J. Schilling, et al., "Simultaneous Endocardial Mapping in the Human Left Ventricle Using a Noncontact Catheter", Circulation, vol. 98, No. 9, Sep. 1, 1998, pp. 887-898, XP055236398.

* cited by examiner

ACCURATE BALLOON COMPUTATION AND VISUALIZATION

FIELD OF THE INVENTION

The present invention relates generally to computing a probe position within a living body, and specifically to improving position measurements.

BACKGROUND

Tracking the position of intrabody probes, such as insertion tubes, catheters and implants, is required for many medical procedures. For example, U.S. Patent Application Publication 2014/0095105 describes an algorithm to correct and/or scale an electrical current-based coordinate system that can include the determination of one or more global transformation or interpolation functions and/or one or more local transformation functions. The global and local transformation functions can be determined by calculating a global metric tensor and a number of local metric tensors. The metric tensors can be calculated based on pre-determined and measured distances between closely-spaced sensors on a catheter.

US Patent Publication 2009/0264738 of Markowitz, et al., describes a volume of a patient being mapped with a system operable to identify a plurality of locations and save a plurality of locations of a mapping instrument. The mapping instrument can include one or more electrodes that can sense a voltage that can be correlated to a three-dimensional location of the electrode at the time of the sensing or measurement. Therefore, a map of a volume can be determined based upon the sensing of the plurality of points without the use of other imaging devices. An implantable medical device can then be navigated relative to the mapping data.

US Patent Publication 2010/0317962 of Jenkins, et al., describes an MRI-compatible catheter that includes an elongated flexible shaft having opposite distal and proximal end portions. A handle is attached to the proximal end portion and includes an actuator in communication with the shaft distal end portion that is configured to articulate the shaft distal end portion. The distal end portion of the shaft may include an ablation tip and includes at least one RF tracking coil positioned adjacent the ablation tip that is electrically connected to an MRI scanner. The at least one RF tracking coil is electrically connected to a circuit that reduces coupling when the at least one RF tracking coil is exposed to an MRI environment. Each RF tracking coil is a 1-10 turn solenoid coil, and has a length along the longitudinal direction of the catheter of between about 0.25 mm and about 4 mm.

U.S. Pat. No. 6,592,520 to Peszynski, et al., describes an ultrasound system and method for intravascular imaging. The ultrasound system includes an intravascular catheter with an ultrasound transducer array, a transmit beamformer, a receive beamformer, and an image generator. The intravascular catheter has an elongated body made for insertion into a blood vessel and connected to a catheter handle. The catheter includes a catheter core located inside a steerable guide sheath, both having a proximal part and a distal part. The catheter includes an articulation region connected to a positioning device for positioning the transducer array to have a selected orientation relative to an examined tissue region. For each orientation of the transducer array, the transmit and receive beamformers acquire ultrasound data over an imaged virtual plane of the examined tissue region. The catheter core is connected to a rotation device constructed and arranged to rotate, or oscillate over an angular range, the transducer array that acquires ultrasound data over a multiplicity of imaged virtual planes. The image generator is constructed to form a selected tissue image based on the acquired ultrasound data.

SUMMARY

By virtue of the disclosure provided herein, we have advanced the technological field of electrophysiology by allowing physicians to observe with greater accuracy of the location of the actual electrodes disposed on a medical probe for navigation as well as for direct control various actual electrode(s) as represented in a virtual 3D environment of a body organ.

Accordingly, there is provided in accordance with an embodiment of the present disclosure a system, including a balloon catheter having a shaft, an inflatable balloon fitted at a distal end of the shaft, and multiple electrodes disposed on the inflatable balloon, a display, and a processor configured to receive signals that are indicative of respective electrode positions of the multiple electrodes in a three-dimensional (3D) space, compute the respective electrode positions of the multiple electrodes based on the received signals, from among a plurality of virtual planes defined by different respective groups of the electrode positions, select a virtual plane that contains a maximum number of the electrode positions to within a given tolerance, fit a circle to points based on the electrode positions that are within the given tolerance of the selected virtual plane, and render to the display a 3D representation of the balloon catheter based on a position and orientation of the fitted virtual circle in the 3D space.

Further in accordance with an embodiment of the present disclosure the processor is configured to compute the plurality of virtual planes from different respective groups of three electrode positions selected from the electrode positions.

Still further in accordance with an embodiment of the present disclosure the processor is configured to remove one electrode position of the electrode positions from the computation of the plurality of virtual planes and from the selection of the virtual plane if the one electrode position is disposed with a given proximity to another one of the electrode positions.

Additionally, in accordance with an embodiment of the present disclosure the processor is configured to merge at least two of the electrode positions for use in the computation of the plurality of virtual planes and the selection of the virtual plane if the at least two electrode positions are within a given proximity.

Moreover, in accordance with an embodiment of the present disclosure the processor is configured to remove one electrode position of the electrode positions from the computation of the plurality of virtual planes and from the selection of the virtual plane if the one electrode position has an associated electrical signal which is less than a given value.

Further in accordance with an embodiment of the present disclosure a multiplicity of virtual planes from the plurality of virtual planes each includes the maximum number of the electrode positions within the given tolerance, the processor being configured to compute for each one virtual plane of the multiplicity of virtual planes, a proximity score of the electrode positions within the given tolerance of the one virtual plane with the one virtual plane, and select one of the multiplicity of virtual planes having a highest proximity score as the selected virtual plane.

Still further in accordance with an embodiment of the present disclosure the processor is configured to compute a new virtual plane from the electrode positions that are within the given tolerance of the selected virtual plane.

Additionally, in accordance with an embodiment of the present disclosure the processor is configured to compute the new virtual plane from the electrode positions that are within the given tolerance of the selected virtual plane using a least-squares-fit method.

Moreover, in accordance with an embodiment of the present disclosure the processor is configured to project the electrode positions that are within the given tolerance of the selected virtual plane onto the new virtual plane and fit the circle to the projected electrode positions.

Further in accordance with an embodiment of the present disclosure the processor is configured to project the electrode positions in a direction perpendicular to the new virtual plane.

Still further in accordance with an embodiment of the present disclosure the processor is configured to compute the respective electrode positions of the multiple electrodes based on the received signals of at least one of magnetic-based location tracking or impedance-based location tracking.

There is also provided in accordance with another embodiment of the present disclosure a method, including receiving signals that are indicative of respective electrode positions of the multiple electrodes in a three-dimensional (3D) space, computing the respective electrode positions of the multiple electrodes based on the received signals, from among a plurality of virtual planes defined by different respective groups of the electrode positions, selecting a virtual plane that contains a maximum number of the electrode positions to within a given tolerance, fitting a circle to points based on the electrode positions that are within the given tolerance of the selected virtual plane, and rendering to a display a 3D representation of the balloon catheter based on a position and orientation of the fitted virtual circle in the 3D space.

Additionally, in accordance with an embodiment of the present disclosure, the method includes computing the plurality of virtual planes from different respective groups of three electrode positions selected from the electrode positions.

Moreover, in accordance with an embodiment of the present disclosure, the method includes removing one electrode position of the electrode positions from the computing of the plurality of virtual planes and from the selecting of the virtual plane if the one electrode position is disposed with a given proximity to another one of the electrode positions.

Further in accordance with an embodiment of the present disclosure, the method includes merging at least two of the electrode positions for use in the computing of the plurality of virtual planes and the selecting of the virtual plane if the at least two electrode positions are within a given proximity.

Still further in accordance with an embodiment of the present disclosure, the method includes removing one electrode position of the electrode positions from the computing of the plurality of virtual planes and from the selecting of the virtual plane if the one electrode position has an associated electrical signal which is less than a given value.

Additionally, in accordance with an embodiment of the present disclosure a multiplicity of virtual planes from the plurality of virtual planes each includes the maximum number of the electrode positions within the given tolerance, the method further including computing for each one virtual plane of the multiplicity of virtual planes, a proximity score of the electrode positions within the given tolerance of the one virtual plane with the one virtual plane, and selecting one of the multiplicity of virtual planes having a highest proximity score as the selected virtual plane.

Moreover, in accordance with an embodiment of the present disclosure, the method includes computing a new virtual plane from the electrode positions that are within the given tolerance of the selected virtual plane.

Further in accordance with an embodiment of the present disclosure the computing the new virtual plane includes computing the new virtual plane from the electrode positions that are within the given tolerance of the selected virtual plane using a least-squares-fit method.

Still further in accordance with an embodiment of the present disclosure, the method includes projecting the electrode positions that are within the given tolerance of the selected virtual plane onto the new virtual plane wherein the fitting includes fitting the circle to the projected electrode positions.

Additionally, in accordance with an embodiment of the present disclosure the projecting includes projecting the electrode positions in a direction perpendicular to the new virtual plane.

Moreover, in accordance with an embodiment of the present disclosure computing the respective electrode positions includes computing the respective positions using at least one of magnetic-based location tracking or impedance-based location tracking.

There is also provided in accordance with still another embodiment of the present disclosure a software product, including a non-transient computer-readable medium in which program instructions are stored, which instructions, when read by a central processing unit (CPU), cause the CPU to receive signals that are indicative of respective electrode positions of the multiple electrodes in a three-dimensional (3D) space, compute the respective electrode positions of the multiple electrodes based on the received signals, from among a plurality of virtual planes defined by different respective groups of the electrode positions, select a virtual plane that contains a maximum number of the electrode positions to within a given tolerance, fit a circle to the electrode positions that are within the given tolerance of the selected virtual plane, and display a 3D representation of the balloon catheter based on a position and orientation of the fitted virtual circle in the 3D space.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
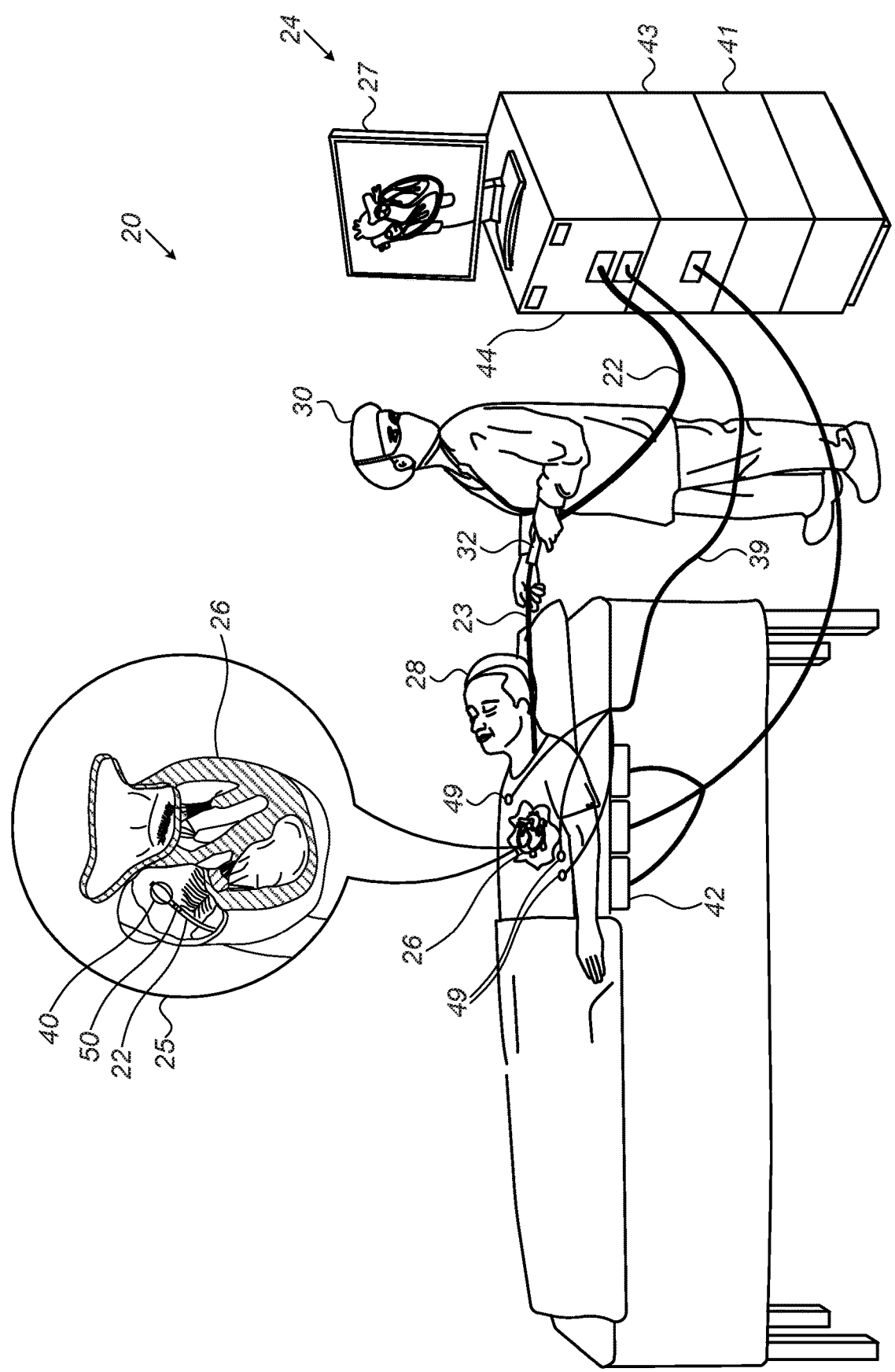
FIG. 1 is a schematic pictorial illustration of a catheter-based position tracking and ablation system in accordance with an embodiment of the present invention.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment. As well, the term "proximal" indicates a location closer to the operator whereas "distal" indicates a location further away to the operator or physician. Finally, the term "virtual" indicates a computer-generated representation of certain objects or abstract geometric indicators.

In order to display an image of a balloon catheter correctly within the heart, the position and orientation of the balloon must be accurately known. The position and orientation of the balloon may be found by finding the positions of each of the electrodes on the balloon and finding a center and radius of a fitted virtual circle surrounding the balloon, assuming the balloon is actually a sphere. The positions may be found using any suitable position measuring system. However, each of the individual electrode positions is noisy, so that images, even after filtration and noise reduction of the electrode positions, also appear to move due to the noise even though the catheter may be steady. A physician performing a medical procedure may then be in doubt as to the current location of the catheter which may slow down the medical procedure and/or lead to serious unwanted results.

Embodiments of the present invention improve computation accuracy of the position and orientation of the balloon so as to reduce noise in a rendered image of the balloon. Using an appropriate positioning system, signals are received that are indicative of respective electrode positions of the electrodes disposed on the balloon in a virtual three-dimensional (3D) space. Electrode positions may be computed from the received signals. While any given electrode has a 3D form, the electrode may be represented by a notional point-position.

As a preparatory step, electrode positions which appear to be spurious, for example, due to faulty electrodes, may be removed or merged for use in the continuation of the analysis described below as the identified "spurious" electrode positions may unduly weight the analysis.

Different virtual planes in 3D space may be defined by different combinations of three electrode positions selected from the computed electrode positions. Each of the virtual planes may be analyzed to calculate the number of electrode positions that are within a given tolerance of the virtual plane. The tolerance may be defined as a given distance from the virtual plane (e.g., ±3 mm or an absolute value of the same) or a given angular displacement from a center of the virtual plane (e.g., ±25 degrees or an absolute value of the same). The virtual plane containing the maximum number of electrode positions is then selected as the virtual plane which includes a circle that best defines an equator of the balloon.

By way of example, for ten electrode positions there may be 120 different sets of three electrode positions, and thus 120 possible virtual planes in 3D space. The remaining seven electrode positions for each of the 120 possible virtual planes are considered, and the 3D virtual plane having the highest number of electrode positions within a given tolerance of that 3D virtual plane is assumed to be the virtual plane which includes the circle that best defines the equator of the balloon.

If there is more than one virtual plane containing the maximum number of electrode positions, then one of the virtual planes (with the maximum number of electrode positions that are within the given tolerance of the virtual plane) could be selected randomly or based on a proximity score measuring the proximity between the virtual plane and the electrode positions that are within the given tolerance of the virtual plane.

The selected virtual plane may then be used as a basis for computing the position and orientation of the balloon. In some embodiments, a new virtual plane is computed from the electrode positions that are within the given tolerance of the selected virtual plane using a fitting algorithm such as a least-squares-fit algorithm. The electrode positions that are within the given tolerance of the selected virtual plane are then projected onto the new virtual plane. In some embodiments, the electrode positions may be projected onto the selected virtual plane.

The system may then fit a virtual circle to the projected electrode positions. The virtual circle has a center position, radius and orientation in 3D space thereby providing the position and orientation of the equator of the balloon in 3D space.

The balloon catheter may be imaged using a graphic processing unit (GPU), based on any suitable method for example, but not limited to, using an imaging method described in US Patent Publication 2018/0182157 of Zar, et al which is herein incorporated by reference. In particular, paragraphs 31 to 48 of the Zar, et al. reference describe rendering quadrics over electroanatomical maps. Examples of quadric surfaces include spheres, ellipsoids, cylinders, cones, hyperbolic paraboloids, paraboloids, and hyperboloids. The imaging may include using mechanical data of splines of the inflatable balloon, may assume that there is material between the splines of the inflatable balloon and combine various quadrics to form an image of the balloon catheter. Other imaging methods based on the mechanical data as well as the position and orientation of the circle may be used to image the balloon catheter.

System Description

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Figure 2:
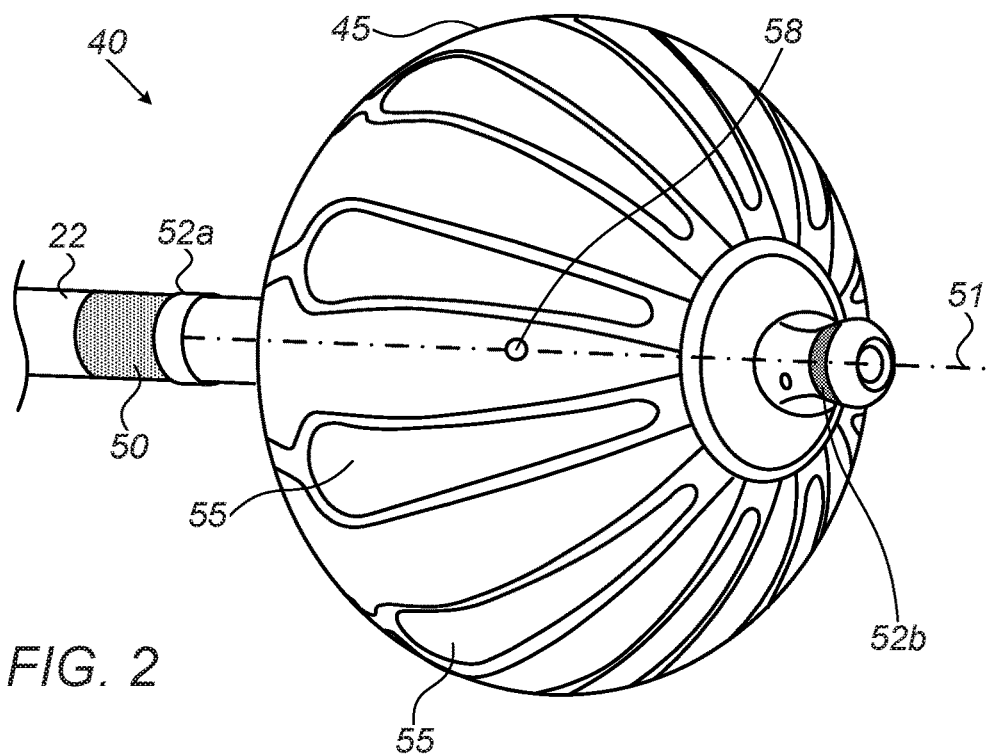
FIG. 2 is a schematic pictorial illustration of a balloon catheter used in the system of FIG. 1.

Reference is now made to FIG. 1, which is a schematic pictorial illustration of a catheter-based position tracking and ablation system 20 in accordance with an embodiment of the present invention. Reference is also made to FIG. 2, which is a schematic pictorial illustration of a balloon catheter 40, in accordance with an embodiment of the present invention.

The position tracking and ablation system 20 is used to determine the position of the balloon catheter 40, seen in an inset 25 of FIG. 1 and in more detail in FIG. 2. The balloon catheter 40 includes a shaft 22 and an inflatable balloon 45 fitted at a distal end of the shaft 22. Typically, the balloon catheter 40 is used for therapeutic treatment, such as spatially ablating cardiac tissue, for example at the left atrium.

The position tracking and ablation system 20 can determine a position and orientation of the shaft 22 of the balloon catheter 40 based on sensing-electrodes 52 (proximal-electrode 52a and distal-electrode 52b) fitted on the shaft 22, on either side of the inflatable balloon 45 and a magnetic sensor 50 fitted just proximally to proximal-electrode 52a. The proximal-electrode 52a, the distal-electrode 52b, and the magnetic sensor 50 are connected by wires running through the shaft 22 to various driver circuitries in a console 24. In some embodiments, the distal-electrode 52b may be omitted.

The shaft 22 defines a longitudinal axis 51. A center point 58 on the axis 51, which is the origin of the sphere shape of the inflatable balloon 45, defines a nominal position of the inflatable balloon 45. Multiple ablation electrodes 55 are disposed in a circumference over the inflatable balloon 45, which occupy a large area as compared with sensing-electrodes 52a and 52b. Radio frequency power may be supplied to the ablation electrodes 55 to ablate the cardiac tissue.

Typically, the disposed ablation electrodes 55 are evenly distributed along an equator of the inflatable balloon 45, where the equator is generally aligned perpendicular to the longitudinal axis 51 of the distal end of the shaft 22.

The illustration shown in FIG. 2 is chosen purely for the sake of conceptual clarity. Other configurations of sensing-electrodes 52 and ablation electrodes 55 are possible. Additional functionalities may be included in the magnetic sensor 50. Elements which are not relevant to the disclosed embodiments of the invention, such as irrigation ports, are omitted for the sake of clarity.

As shown in FIG. 1, a physician 30 navigates the balloon catheter 40 to a target location in a heart 26 of a patient 28 by manipulating the shaft 22 using a manipulator 32 near the proximal end of the catheter and/or deflection from a sheath 23. The balloon catheter 40 is inserted, while the inflatable balloon 45 is deflated, through the sheath 23, and only after the balloon catheter 40 is retracted from the sheath 23 is the inflatable balloon 45 inflated and regains its intended functional shape. By containing balloon catheter 40 in a deflated configuration, the sheath 23 also serves to minimize vascular trauma on its way to the target location.

Console 24 comprises a processor 41, typically a general-purpose computer and a suitable front end and interface circuits 44 for generating signals in, and/or receiving signals from, surface electrodes 49 which are attached by wires running through a cable 39 to the chest and to the back of the patient 28.

Console 24 further comprises a magnetic-sensing subsystem. The patient 28 is placed in a magnetic field generated by a pad containing magnetic field generator coils 42, which are driven by a unit 43 disposed in the console 24. The magnetic fields generated by the coils 42 generate direction signals in the magnetic sensor 50, which are then provided as corresponding electrical inputs to the processor 41.

In some embodiments, the processor 41 uses the position-signals received from the sensing-electrodes 52, the magnetic sensor 50 and the ablation electrodes 55 to estimate a position of the balloon catheter 40 inside an organ, such as inside a cardiac chamber. In some embodiments, the processor 41 correlates the position signals received from the electrodes 52, 55 with previously acquired magnetic location-calibrated position signals, to estimate the position of the balloon catheter 40 inside a cardiac chamber. The position coordinates of the sensing-electrodes 52a and 52b (referenced together here as "52") and the ablation electrodes 55 may be determined by the processor 41 based on, among other inputs, measured impedances, or on proportions of currents distribution, between the electrodes 52, 55 and the surface electrodes 49. The console 24 drives a display 27, which shows the distal end of the catheter position inside the heart 26.

The method of position sensing using current distribution measurements and/or external magnetic fields is implemented in various medical applications, for example, in the Carto® system, produced by Biosense Webster Inc. (Irvine, Calif.), and is described in detail in U.S. Pat. Nos. 5,391,199, 6,690,963, 6,484,118, 6,239,724, 6,618,612, 6,332,089, 7,756,576, 7,869,865, and 7,848,787, in PCT Patent Publication WO 96/05768, and in U.S. Patent Application Publications 2002/0065455 A1, 2003/0120150 A1 and 2004/0068178 A1, whose disclosures are all incorporated herein by reference.

The Carto®3 system applies an Active Current Location (ACL) impedance-based position-tracking method. In some embodiments, using the above noted ACL method, the processor 41 estimates the positions of the sensing-electrodes 52 and the ablation electrodes 55. In some embodiments, the signals received from the electrodes 52, 55 are correlated with a matrix which maps impedance (or another electrical value) measured by the sensing-electrodes 52, 55 with a position of that was previously acquired from magnetic location-calibrated position signals.

In some embodiments, to visualize catheters which do not include a magnetic sensor, the processor 41 may apply an electrical signal-based method, referred to as the Independent Current Location (ICL) method. In the ICL method, the processor 41 calculates a local scaling factor for each voxel of a volume of the balloon catheter 40. The factor is determined using a catheter with multiple electrodes having a known spatial relationship, such as a Lasso-shaped catheter. However, although yielding accurate local scaling (e.g., over several millimeters), ICL is believed to be less accurate when applied to a balloon catheter, whose size is on the order of centimeters. The position-signals generated by the ablation electrodes 55 are believed to be typically too coarse to be useful on their own (e.g., they are spread in space due to the large area of ablation-electrodes). The ICL method, in which positions are calculated based on current distribution proportions may have errors and may yield a distorted shape of the balloon catheter 40, due to the non-linear nature of the current-based ICL space. In some embodiments, the processor 41 may apply the disclosed ICL method to scale the balloon catheter shape into a correct one, based on known smaller scale distances between electrodes of a lasso-shaped catheter, as well as based on larger scale distances, themselves based on the known distance between the sensing-electrodes 52 at the ends of the inflatable balloon 45.

In many cases, using the ICL, ACL and/or magnetic location methods may not be accurate enough to determine an exact position and orientation of the inflatable balloon 45 without noise. As such we have devised the technical solutions to overcome possible shortcomings of the existing system.

FIG. 1 shows only elements related to the disclosed techniques, for the sake of simplicity and clarity. The system 20 typically comprises additional modules and elements that are not directly related to the disclosed techniques, and thus are intentionally omitted from FIG. 1 and from the corresponding description.

Figure 3:
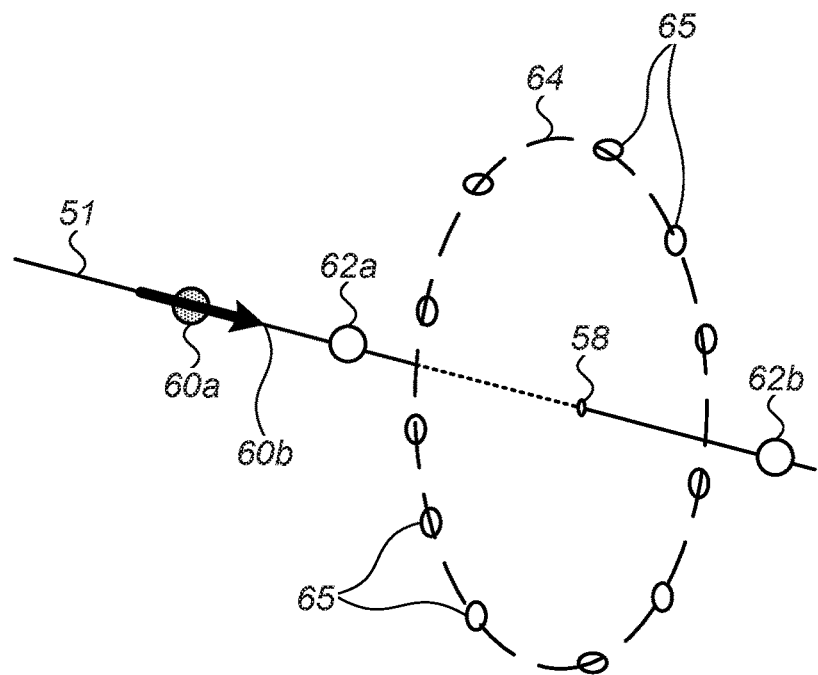
FIG. 3 is a schematic pictorial illustration of various datum points over the balloon catheter of FIG. 2.

Reference is now made to FIG. 3, which is a schematic pictorial illustration of various datum points over the balloon catheter 40 of FIG. 2, in accordance with an embodiment of the present invention. The location of the datum points may be presented, for example, in a coordinate system defined for the electroanatomical map stored in the processor 41, to which the system 20 correlates the position in space of the balloon 40.

FIG. 3 shows that the actual proximal-electrode 52a is located at a virtual position 62a, while actual distal electrode 52b is located at a virtual position 62b. The actual physical magnetic sensor 50 is located at a virtual position 60a, while, as described above, the sensor 50 is capable of indicating a virtual direction 60b, which is parallel to the direction of shaft 22 (i.e., parallel to the axis 51). Despite the large areas of actual ablation electrodes 55, a consistent and useful general representation of the electrodes 55 in space is possible, in the form of virtual electrode positions 65 on a virtual circle 64 (forming an equator of the inflatable balloon 45) embedded in a virtual plane orthogonal to the axis 51. In other words, when the balloon is fully inflated, the virtual electrode positions 65 should ideally lay on the virtual circle 64 which has the maximal transverse diameter of the inflatable balloon 45 (FIG. 2). A nominal position of the inflatable balloon 45 is ideally defined by center point 58, which is also the center of the circle 64. Assuming, the virtual electrode positions 65 provide accurate and meaningful data of the position of the actual physical ablation electrodes 55, the virtual electrode positions 65 and the virtual circle 64 that they define may be used to compute the position and orientation of the inflatable balloon 45. However, each of the individual electrode positions are generally noisy (as discussed above) and therefore the locations 65 generally do not conveniently fall on the virtual circle 64.

Figure 4A:
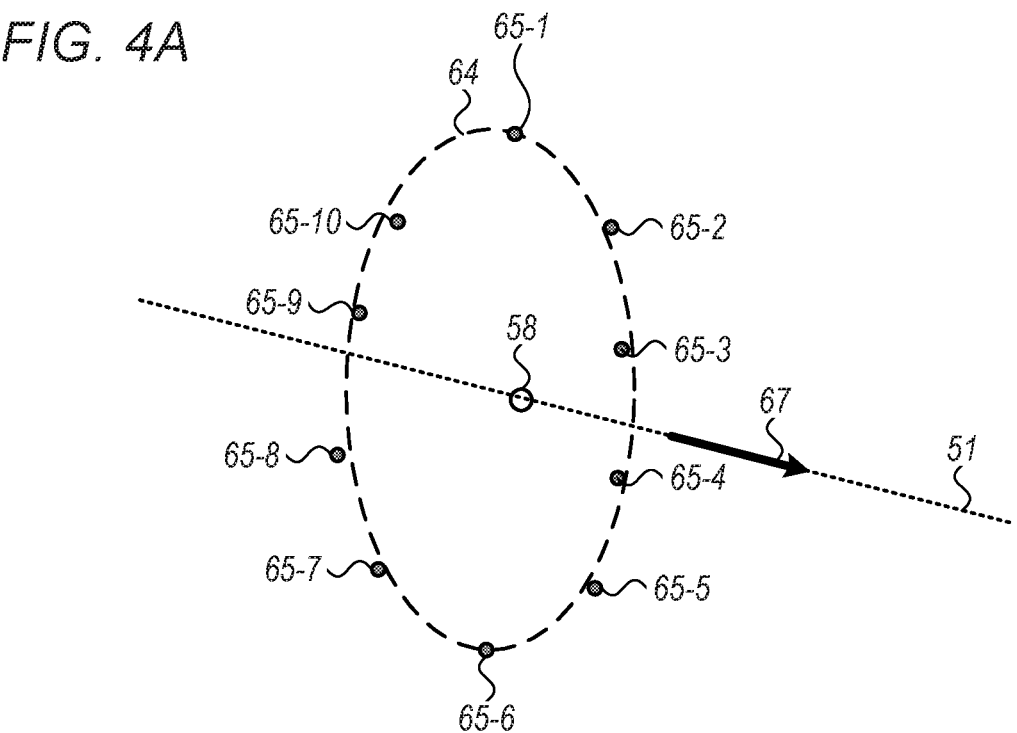
FIGS. 4A and 4B are alternative schematic pictorial illustrations of various datum points over the balloon catheter of FIG. 2.
Figure 4B:
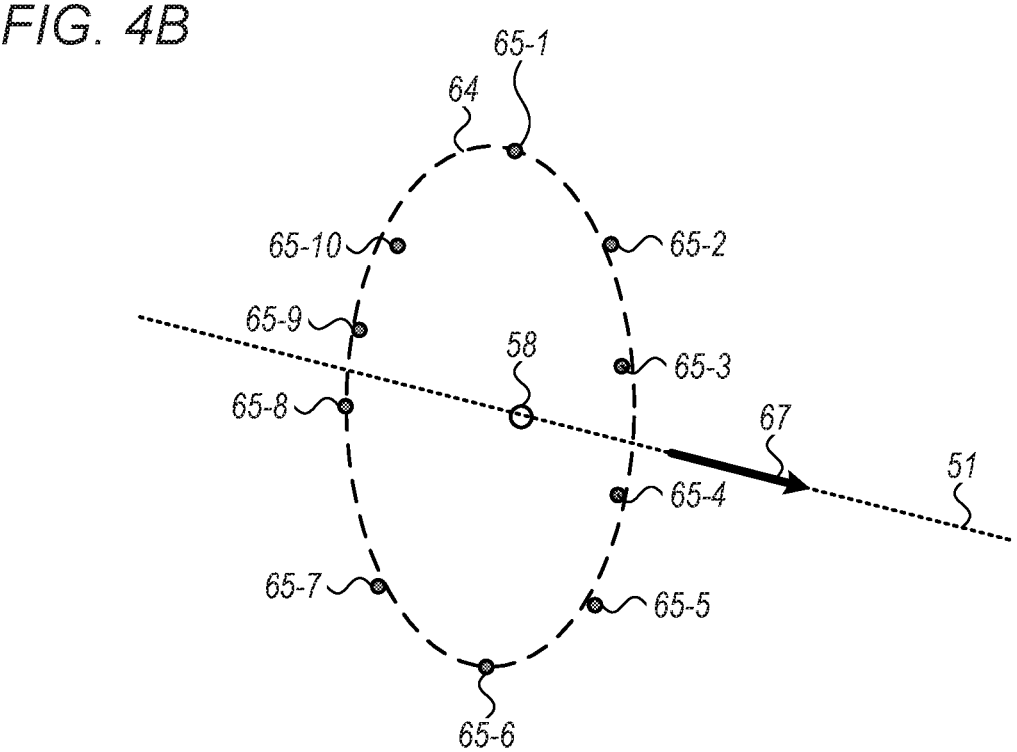

Reference is now made to FIGS. 4A and 4B, which are alternative schematic pictorial illustrations of various datum points over the balloon catheter 40 of FIG. 2. FIGS. 4A and 4B show that the virtual electrode positions 65 are in fact noisy and may fall inside the virtual circle 64 towards the center point 58, and/or outside the circle away from the center point 58, and/or either side of the virtual circle 64 in one direction (arrow 67) along the longitudinal axis 51, and/or in another direction along the longitudinal axis 51.

FIG. 4A also shows that virtual electrode position 65-10 is not as evenly spaced as the other virtual electrode positions 65 and may indicate the ablation electrode 55 associated with the virtual electrode position 65-10 is burnt or the virtual electrode position 65-10 is otherwise spurious. Therefore, the virtual electrode position 65-10 may not be reliably used in computing the position and orientation of the virtual circle 64.

FIG. 4B also shows that electrode positions 65-8, 65-9, 65-10 are closely spaced together and therefore those electrode positions may not be reliably used in computed the position and orientation of the virtual circle 64. In some embodiments, the electrode positions 65-8, 65-9, 65-10 may be removed from computations computing the virtual circle 64. In other embodiments, the electrode positions 65-8, 65-9, 65-10 may be averaged to provide a mean electrode position for use in computations computing the virtual circle 64.

Figure 5:
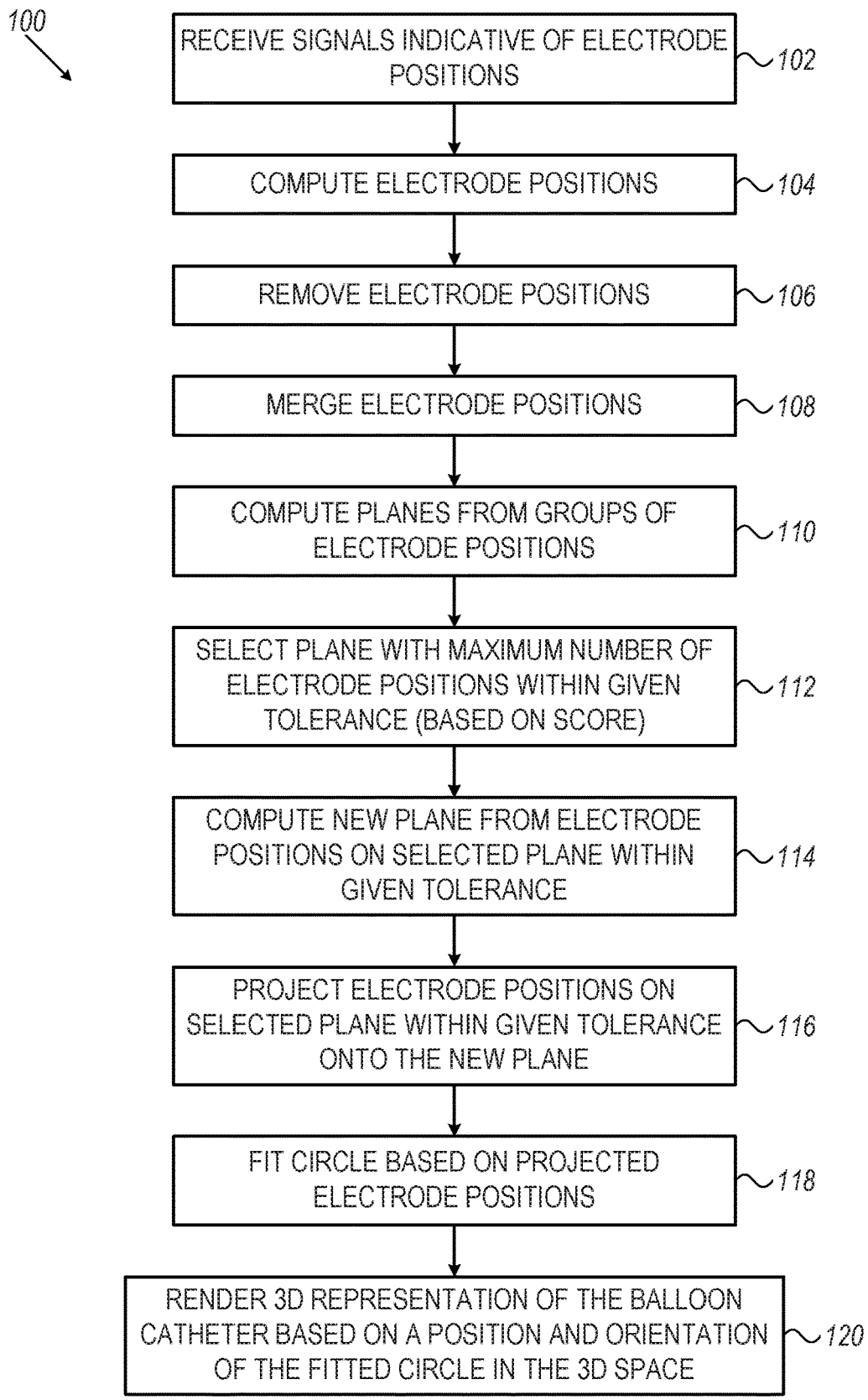
FIG. 5 is a flowchart including exemplary steps in a method of operation of the system of FIG. 1.

Reference is now made to FIG. 5, which is an algorithm 100 in the form of a flow chart for a series of exemplary instruction steps to enable one skilled in the art to write computer codes to transform a general-purpose computer or CPU into a special processor unit 41 to perform the method of operation for system 20 of FIG. 1. Processor 41 is typically programmed by a skilled programmer in software codes to carry out the algorithm described herein. The software may be downloaded to the computer in electronic form, over a network, for example, or it may, alternatively or additionally, be provided and/or stored on non-transitory tangible media, such as magnetic, optical, or electronic memory. With reference to FIGS. 1, 2 and algorithm 100 of FIG. 5, the processor 41 is configured or programmed to receive (step 102) signals that are indicative of respective virtual electrode positions 65 (FIGS. 3-4) of the multiple electrodes 55 in a three-dimensional (3D) space. In a preferred embodiment, step 102 is typically initiated after expansion or inflation of the balloon.

The processor 41 is configured or programmed to compute (step 104) the respective virtual electrode positions 65 of the multiple electrodes 55 based on the received signals. As described above with reference to FIGS. 1 and 2, the virtual electrode positions 65 may be computed using any suitable position tracking system based on any suitable position tracking method, for example, but not limited to, using magnetic-based location tracking and/or impedance-based location tracking (such as ICL or ACL).

As a preparatory step, virtual electrode positions 65 which appear to be spurious, for example, due to faulty electrodes (e.g., burnt electrodes), may be removed or merged for use in the continuation of the analysis described below. The identified "spurious" electrode positions may unduly weight the analysis.

Therefore, in some embodiments, the processor 41 is configured or programmed to remove (step 106) one (or more) electrode position(s) 65 from the computation of the plurality of virtual planes (described below) and from the selection of the virtual plane (described below) if the electrode position(s) 65 is disposed with a given proximity to another one of the electrode positions 65. The example shown in FIG. 4A shows that the virtual electrode position 65-10 is within the given proximity of the virtual electrode position 65-9. An example range of the given proximity is 0-7 mm. However, the given proximity may depend on various factors including the size of the inflatable balloon 45, the number of ablation electrodes 55, how often the virtual electrode positions 65 are sampled, and/or a required accuracy.

Similarly, in some embodiments, the processor 41 may be configured to merge (step 108) two or more of the virtual electrode positions 65 (for example, the electrode positions 65-8, 65-9, 65-10) for use in the computation of the plurality of virtual planes and the selection of the virtual plane if the two or more virtual electrode positions 65 are within a given proximity. An example range of the given proximity in which all the mergeable virtual electrode positions 65 would fall to result in merging of those virtual electrode positions 65 is 0-7 mm. However, the given proximity may depend on various factors including the size of the inflatable balloon 45, the number of ablation electrodes 55, how often the virtual electrode positions 65 are sampled, and/or a required accuracy. When the virtual electrode positions 65 are merged, the average position of the merged virtual electrode positions 65 is used in the computation of the plurality of virtual planes and the selection of the virtual plane described below.

In some embodiments, the processor 41 is programmed to remove a virtual electrode position 65 from the computation of the plurality of virtual planes and from the selection of the virtual plane if the virtual electrode position 65 has an associated electrical signal which is less than a given value possibly indicative of a faulty (e.g., burnt) electrode 65. The given value may be in any suitable range, for example, less than 30% to 70% of the average electrical signal measured from the other ablation electrodes 55.

Different virtual planes in 3D space may be defined by different combinations of three electrode positions selected from the computed electrode positions 65. Each of the virtual planes may be analyzed to calculate the number of electrode positions that are within a given tolerance of the virtual plane. The tolerance may be defined as a given distance from the virtual plane (e.g., ±3 mm or the absolute value of the same value) or a given angular displacement from a center of the virtual plane (e.g., ±25 degrees or the absolute value of the same value). The center of the virtual plane may be computed or estimated from an average position of the virtual electrode positions 65 or based on the known or expected positions 60a, 62a, and/or 62b (FIG. 3) on the shaft 22.

Therefore, the processor 41 may be configured to compute (step 110) a plurality of virtual planes (not shown) from different respective groups of three virtual electrode positions 65 selected from the electrode positions 65. The processor 41 may then compute, for each virtual plane, the number of virtual electrode positions 65 within the given tolerance of that virtual plane. The processor 41 may also compute, for each virtual plane, a proximity score of the virtual electrode positions 65 within the given tolerance of that virtual plane. The proximity score may be computed based on any suitable value of proximity, for example, but not limited to, squaring the distances of the virtual electrode positions 65 from the virtual plane or a root mean square proximity method.

Although the embodiments that are described in detail use groups of three virtual electrode positions 65 to define the virtual planes, virtual planes could alternatively be defined by groups of four or more electrodes.

The processor 41 is configured or programmed, from among the plurality of virtual planes defined by the different respective groups of the electrode positions 65, to select (step 112) a virtual plane that contains the maximum number of the virtual electrode positions 65 to within the given tolerance.

If there is more than one "maximum" virtual plane including the maximum number of the virtual electrode positions 65 to within the given tolerance, the processor 41 may be configured to select one of the "maximum" virtual planes having a highest proximity score as the selected virtual plane. In some embodiments, the processor 41 may be configured to select one the "maximum" virtual planes randomly.

By way of example, for ten virtual electrode positions 65 there may be 120 different sets of three electrode positions 65, and thus 120 possible virtual planes in 3D space. The remaining seven virtual electrode positions 65 for each of the 120 possible virtual planes are considered, and the 3D virtual plane having the highest number of virtual electrode positions 65 within a given tolerance of that 3D virtual plane is assumed to be the virtual plane which includes the virtual circle 64 that best defines the equator of the inflatable balloon 45.

The selected virtual plane may then be used as a basis for computing the position and orientation of the inflatable balloon 45. In some embodiments, the processor 41 is configured or programmed to compute (step 114) a new virtual plane from the virtual electrode positions 65 that are within the given tolerance of the selected virtual plane. In some embodiments, the processor 41 is configured or programmed to compute the new virtual plane from the electrode positions that are within the given tolerance of the selected virtual plane using a least-squares-fit method or any other suitable virtual plane fitting algorithm. Computing the new virtual plane may provide more accurate results as the computation uses the virtual electrode positions 65 that are within the given tolerance of the selected virtual plane (and not the virtual electrode positions 65 outside of the given tolerance).

In embodiments where the new virtual plane is computed, the processor 41 may be configured to project (step 116) the virtual electrode positions 65 that are within the given tolerance of the selected virtual plane onto the new virtual plane. In some embodiments, the processor 41 is configured or programmed to project the virtual electrode positions 65 in a direction perpendicular to the new virtual plane.

In other embodiments, the steps of steps 114 and 116 are replaced by the processor 41 projecting the virtual electrode positions 65 that are within the given tolerance of the selected virtual plane onto the selected virtual plane.

The processor 41 is configured or programmed to fit (step 118) a virtual circle (which generally corresponds to the virtual circle 64 subjects to computation deviations due to accuracy of the electrode positions 65) to points based on the virtual electrode positions 65 that are within the given tolerance of the selected virtual plane. In some embodiments the processor 41 is configured or programmed to fit the circle to the projected electrode positions (projected onto the selected virtual plane or onto the new virtual plane). The fitted virtual circle has a center position, radius and orientation in 3D space thereby providing the position and orientation of the equator of the inflatable balloon 45 in 3D space.

The processor 41 is configured or programmed to render (step 120), to the display 27, a virtual 3D representation of the balloon catheter 40 based on a position and orientation of the fitted virtual circle in the 3D space. The rendering of the 3D representation of the balloon catheter 40 is now described below in more detail with reference to FIGS. 6A and 6B.

Figure 6A:
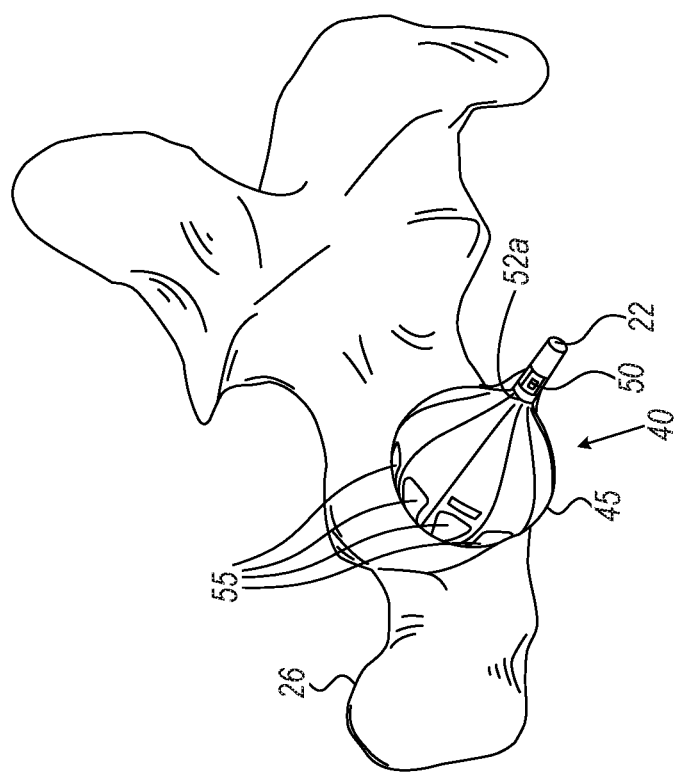
FIGS. 6A and 6B are schematic views of a respective 3D rendered image of the balloon catheter inside a chamber of a heart that a healthcare provider would see in order to navigate to a desired tissue location in the heart (or any body tissue).
Figure 6B:
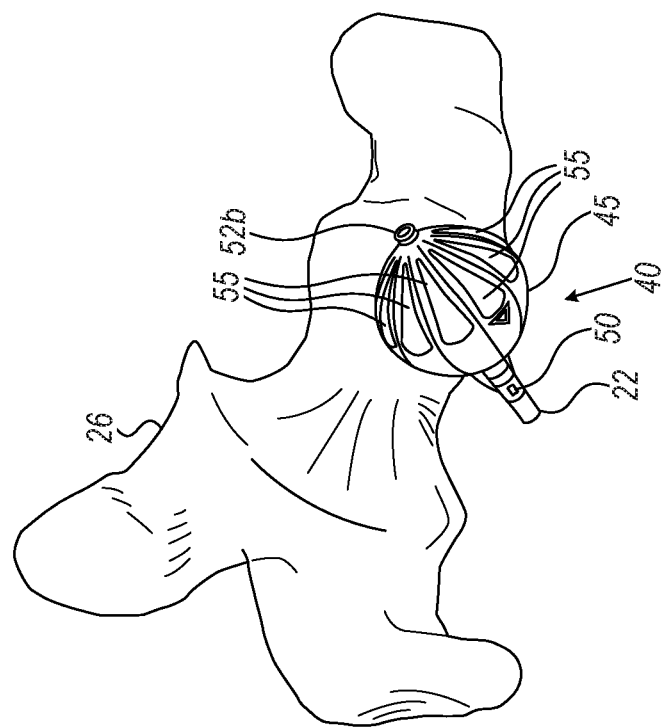

Reference is now made to FIGS. 6A and 6B which are schematic views of a respective 3D rendered image of the balloon catheter 40 inside a chamber of the heart 26 on a display 27. The balloon catheter 40 may be imaged using a graphic processing unit (GPU), based on any suitable method for example, but not limited to, using an imaging method described in US Patent Publication 2018/0182157 of Zar, et al. In particular, paragraphs 31 to 48 of the Zar, et al. reference describe rendering quadrics over electroanatomical maps. Examples of quadric surfaces include spheres, ellipsoids, cylinders, cones, hyperbolic paraboloids, paraboloids, and hyperboloids. The imaging may include using mechanical data of splines of the inflatable balloon 45, may assume that there is material between the splines of the inflatable balloon 45 and combine various quadrics to form an image of the balloon catheter. Other imaging methods based on the mechanical data as well as the position and orientation of the circle may be used to image the balloon catheter 40.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:

1. A system, comprising:
    a balloon catheter having a shaft, an inflatable balloon fitted at a distal end of the shaft, and multiple electrodes disposed on the inflatable balloon;
    a display; and
    a processor configured to:
        receive signals that are indicative of respective electrode positions of the multiple electrodes in a three-dimensional (3D) space;
        compute the respective electrode positions of the multiple electrodes based on the received signals;
        from among a plurality of virtual planes defined by different respective groups of the electrode positions, select a virtual plane that contains a maximum number of the electrode positions to within a given tolerance;
        fit a circle to points based on the electrode positions that are within the given tolerance of the selected virtual plane; and
        render to the display a 3D representation of the balloon catheter based on a position and orientation of the fitted virtual circle in the 3D space.

2. The system according to claim 1, wherein the processor is configured to compute the plurality of virtual planes from different respective groups of three electrode positions selected from the electrode positions.

3. The system according to claim 1, wherein the processor is configured to remove one electrode position of the electrode positions from the computation of the plurality of virtual planes and from the selection of the virtual plane if the one electrode position is disposed with a given proximity to another one of the electrode positions.

4. The system according to claim 1, wherein the processor is configured to merge at least two of the electrode positions for use in the computation of the plurality of virtual planes and the selection of the virtual plane if the at least two electrode positions are within a given proximity.

5. The system according to according to claim 1, wherein the processor is configured to remove one electrode position of the electrode positions from the computation of the plurality of virtual planes and from the selection of the virtual plane if the one electrode position has an associated electrical signal which is less than a given value.

6. The system according to according to claim 1, wherein a multiplicity of virtual planes from the plurality of virtual planes each includes the maximum number of the electrode positions within the given tolerance, the processor being configured to: compute for each one virtual plane of the multiplicity of virtual planes, a proximity score of the electrode positions within the given tolerance of the one virtual plane with the one virtual plane; and select one of the multiplicity of virtual planes having a highest proximity score as the selected virtual plane.

7. The system according to according to claim 1, wherein the processor is configured to compute a new virtual plane from the electrode positions that are within the given tolerance of the selected virtual plane.

8. The system according to claim 7, wherein the processor is configured to compute the new virtual plane from the electrode positions that are within the given tolerance of the selected virtual plane using a least-squares-fit method.

9. The system according to claim 7, wherein the processor is configured to:
    project the electrode positions that are within the given tolerance of the selected virtual plane onto the new virtual plane; and
    fit the circle to the projected electrode positions.

10. The system according to claim 1, wherein the processor is configured to project the electrode positions in a direction perpendicular to the new virtual plane.

11. The system according to claim 1, wherein the processor is configured to compute the respective electrode positions of the multiple electrodes based on the received signals of at least one of magnetic-based location tracking or impedance-based location tracking.

12. A method to display a representation of an expandable medical probe in body tissue, the medical probe including a balloon catheter having a shaft with an inflatable balloon fitted at a distal end of the shaft, and multiple electrodes disposed on the inflatable balloon, the method comprising the steps of:
    receiving signals that are indicative of respective electrode positions of the multiple electrodes in a three-dimensional (3D) space;
    computing the respective electrode positions of the multiple electrodes based on the received signals;
    from among a plurality of virtual planes defined by different respective groups of the electrode positions, selecting a virtual plane that contains a maximum number of the electrode positions to within a given tolerance;
    fitting a circle to points based on the electrode positions that are within the given tolerance of the selected virtual plane; and
    displaying a 3D representation of the balloon catheter based on a position and orientation of the fitted virtual circle in the 3D space.

13. The method according to claim 12, further comprising computing the plurality of virtual planes from different respective groups of three electrode positions selected from the electrode positions.

14. The method according to claim 12, further comprising removing one electrode position of the electrode positions from the computing of the plurality of virtual planes and from the selecting of the virtual plane if the one electrode position is disposed with a given proximity to another one of the electrode positions.

15. The method according to claim 12, further comprising merging at least two of the electrode positions for use in the computing of the plurality of virtual planes and the selecting of the virtual plane if the at least two electrode positions are within a given proximity.

16. The method according to claim 12, further comprising removing one electrode position of the electrode positions from the computing of the plurality of virtual planes and from the selecting of the virtual plane if the one electrode position has an associated electrical signal which is less than a given value.

17. The method according to claim 12, wherein a multiplicity of virtual planes from the plurality of virtual planes each includes the maximum number of the electrode positions within the given tolerance, the method further comprising computing for each one virtual plane of the multiplicity of virtual planes, a proximity score of the electrode positions within the given tolerance of the one virtual plane with the one virtual plane; and selecting one of the multiplicity of virtual planes having a highest proximity score as the selected virtual plane.

18. The method according to claim 12, further comprising computing a new virtual plane from the electrode positions that are within the given tolerance of the selected virtual plane.

19. The method according to claim 12, wherein the computing the new virtual plane includes computing the new virtual plane from the electrode positions that are within the given tolerance of the selected virtual plane using a least-squares-fit method.

20. The method according to claim 12, further comprising projecting the electrode positions that are within the given tolerance of the selected virtual plane onto the new virtual plane wherein the fitting includes fitting the circle to the projected electrode positions.

21. The method according to claim 20, wherein the projecting includes projecting the electrode positions in a direction perpendicular to the new virtual plane.

22. The method according to claim 12, wherein computing the respective electrode positions includes computing the respective positions using at least one of magnetic-based location tracking or impedance-based location tracking.

23. A software product, comprising a non-transient computer-readable medium in which program instructions are stored, which instructions, when read by a central processing unit (CPU), cause the CPU to:
receive signals that are indicative of respective electrode positions of multiple electrodes of a medical probe disposed in a three-dimensional (3D) space;
compute the respective electrode positions of the multiple electrodes based on the received signals;
from among a plurality of virtual planes defined by different respective groups of the electrode positions, select a virtual plane that contains a maximum number of the electrode positions of the medical probe to within a given tolerance;
fit a circle to the electrode positions of the medical probe that are within the given tolerance of the selected virtual plane; and
display a 3D representation of the medical probe based on a position and orientation of the fitted virtual circle in the 3D space.

\* \* \* \* \*